United States Patent
Schröter et al.

(10) Patent No.: US 11,479,631 B2
(45) Date of Patent: Oct. 25, 2022

(54) COMPOSITION CONTAINING MODIFIED BISPHENOL F

(71) Applicant: Hexion GmbH

(72) Inventors: Stephan Schröter, Essen (DE); Pravin Kukkala, Louisville, KY (US); Ganapathy Viswanathan, Louisville, KY (US); Anthony Maiorana, Louisville, KY (US); Athina Kerkaidou, Iserlohn (DE)

(73) Assignee: BAKELITE GMBH ( * ) Notice: Subject to any disclaimer, the term of this patent is extended or adjusted under 35 U.S.C. 154(b) by 0 days.

(21) Appl. No.: 17/059,988

(22) PCT Filed: May 28, 2019

(86) PCT No.: PCT/EP2019/063874
§ 371 (c)(1),
(2) Date: Nov. 30, 2020

(87) PCT Pub. No.: WO2019/229087
PCT Pub. Date: Dec. 5, 2019

(65) Prior Publication Data
US 2021/0230342 A1 Jul. 29, 2021

(30) Foreign Application Priority Data
May 30, 2018 (EP) .................................. 18175075

(51) Int. Cl.
C08G 18/32 (2006.01)
C07C 39/10 (2006.01)
C07C 39/16 (2006.01)
C08G 65/26 (2006.01)
C07C 43/205 (2006.01)
C07C 43/23 (2006.01)

(52) U.S. Cl.
CPC .......... *C08G 18/3215* (2013.01); *C07C 39/10* (2013.01); *C07C 39/16* (2013.01); *C08G 65/2612* (2013.01)

(58) Field of Classification Search
None
See application file for complete search history.

(56) References Cited

U.S. PATENT DOCUMENTS 4,261,922 A * 4/1981 Kern ...................... C07C 41/16
562/77

FOREIGN PATENT DOCUMENTS

JP 03250046 A * 11/1991

* cited by examiner

Primary Examiner — Randy P Gulakowski
Assistant Examiner — Ha S Nguyen
(74) Attorney, Agent, or Firm — Edmonds & Cmaidalka, P.C.

(57) ABSTRACT

The invention relates to a composition that contains a binary mixture of bisphenol F and propoxylated bisphenol F. The aim of the invention is to provide aromatic polyols for preparing polyurethane-based and polyisocyanurate-based polymers, which ensure good handling from a technical point of view and good miscibility with the isocyanate component and render the end product flameproof. For this purpose, the invention devises a composition, which contains a binary mixture of ethoxylated bisphenol F and propoxylated bisphenol F in a weight ratio of 20:80 to 80:20.

11 Claims, No Drawings

COMPOSITION CONTAINING MODIFIED BISPHENOL F

BACKGROUND OF THE INVENTION

In the production of polyurethanes, and polyisocyanurates, isocyanates are crosslinked by a polyaddition reaction using polyols. The isocyanates comprise at least two —NCO groups and the polyols at least two reactive —OH groups (polyhydric alcohols}. Polymers are formed which depending on their chemical or morphological construction may exhibit thermoplastic, elastic or thermosetting properties. Accordingly, polyurethanes and polyisocyanurates have a very wide field of application, for example for foams, coatings, adhesives, elastomers, insulations and composite materials. Particularly in the search for energy- and resource-efficient materials, polyurethanes and polyisocyanurates are particularly important on account of easy-to-realize lightweight construction.

The production of polyurethanes and polyisocyanurates is effected by mixing the polyols with isocyanates, thus causing the system to start to gel after a short time. It will be appreciated that the components need to be matched to one another in terms of their viscosities in order to achieve high degree of mixing that results in homogeneous products having desired properties. The properties of the end-product are substantially determined by the chain length and degree of branching of the polyol component and combinations of different polyols are therefore often employed, for example polyether polyols and polyester polyols, to optimize processing and properties.

During the production of typical rigid polyurethane foams, the highly exothermic reaction between polyols and isocyanates leads to internal scorching. This phenomenon adversely affects the physical properties of the foam and increases the potential for causing problems with respect to the flammability. Moreover, the use of hydrocarbon based organic blowing agents further increases the flammability of the finished foams. Consequently, flame retardant additives are added in the formulation, wherein these are generally halogenated compounds. However, many such flame-retardants pose threat to the environment. Hence, it is desirable to use polyols that are inherently flame resistant, which will enhance the thermal and fire performance of the polyurethane (PUR) and polyisocyanurate (PIR) foams and potentially minimize the amounts of these environmentally and expensive flame retardant additives in the formulation.

Alkoxylated bisphenols are known for the production of polyurethanes. Thus, EP 0 763 067 81 describes the use of alkoxylated bisphenol for the production of hot melt adhesives and EP 2 743 285 A1 for coated conducting elements. It is further apparent from EP 1 851 261 B1 that one component of a two-component polyurethane composition for structural adhesives may be an ethoxylated or propoxylated aromatic diol in combination with aliphatic triols.

However, it has been found that aromatic dial type polyols based on bisphenol A have only insufficient suitability for the production of polyurethanes since they are solid substances which is very disadvantageous in terms of process engineering and in addition also have poor heat resistance.

It has also been found that the use of both pure ethoxylated bisphenol F and pure propoxylated bisphenol F as aromatic diols for the production of polyurethanes face some serious challenges. This is because both are pasty substances which are not pumpable at 20-30 C and thus do not have the desired processability in polyurethane production. Melting of the ethoxylated bisphenol F or of the propoxylated bisphenol F entails an energy input into the system which is also not desired. Furthermore, attempts at solubilizing pure ethoxylated bisphenol F and also pure propoxylated bisphenol F showed that they could not be dissolved in suitable solvents since they had a ready propensity for crystallization.

SUMMARY OF THE INVENTION

It is accordingly an object of the present invention to provide aromatic polyols for the production of polyurethane- and polyisocyanurate-based polymers which ensure good processability at about 20° C. and good miscibility with the isocyanate component and also impart the end product with good flame retardancy, thus making it possible to eschew the use of halogenated compounds.

This object is achieved in accordance with the invention by a composition containing a binary mixture of ethoxylated bisphenol F (EBF) and propoxylated bisphenol F (PBF) in a weight ratio of 20:80 to 80:20.

DETAILED DESCRIPTION OF THE INVENTION

The term binary mixture is herein to be understood as meaning a purely physical mixture of two separate components, namely ethoxylated bisphenol F and propoxylated bisphenol F. Alkoxylated bisphenol F formed by reaction of an ethoxylating agent and propoxylating agent with bisphenol F and thus constituting a co-condensate shall accordingly not be encompassed by the term "binary mixture".

It was found that, surprisingly, binary mixtures of ethoxylated bisphenol F and propoxylated bisphenol F in a weight ratio of 20:80 to 80:20 are exceptionally soluble in various solvents which are also miscible with isocyanates. This was unexpected since—as mentioned above—both ethoxylated bisphenol F and propoxylated bisphenol F have a ready propensity for crystallization.

The bisphenol Fused for the production of ethoxylated or propoxylated bisphenol F is known from the prior art. It is thus produced by reaction of phenol with formaldehyde under acidic conditions. This affords an isomer mixture of o-o', o-p and p-p' bisphenol F which depending on the reaction conditions and production processes can vary in its composition. The hydroxyl functionality of the produced bisphenol F is at least 2.

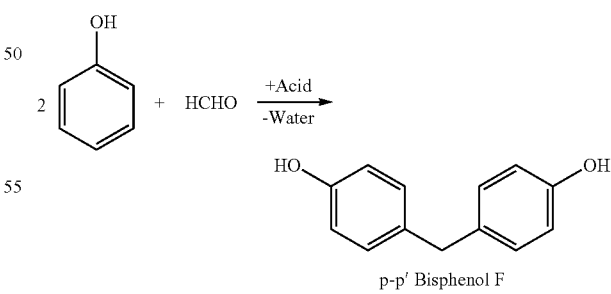

p-p' Bisphenol F

Reaction of the bisphenol F with ethoxylating agents, such as ethylene oxide or ethylene carbonate, affords the ethoxylated bisphenol F. The reaction of the bisphenol F with propoxylating agents, such as propylene oxide or propylene carbonate, to afford the propoxylated bisphenol F is effected in corresponding fashion. Since the reaction with ethylene oxide/propylene oxide, which are in the gaseous state, must be effected in a pressure reactor, which involves more effort from a process engineering point of view, it is preferable to employ ethylene carbonate as the ethoxylating agent/propylene carbonate as the propoxylating agent.

The reaction shall be elucidated using the example of p-p' Bisphenol F:

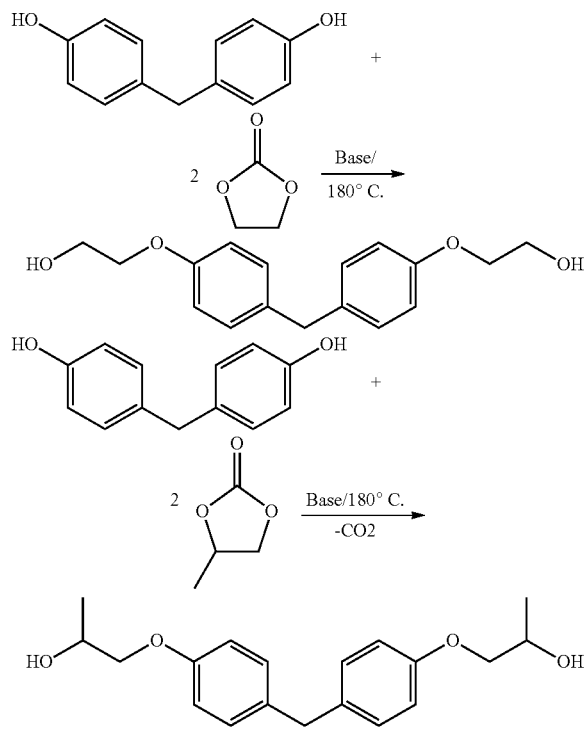

On account of the different isomers of bisphenol F corresponding isomers of the ethoxylated/propoxylated product are also formed:

Isomers of the ethoxylated bisphenol F Isomers of the propoxylated bisphenol F

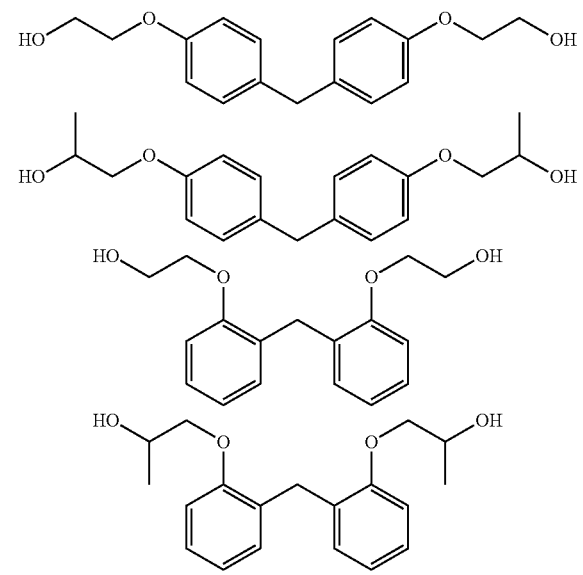

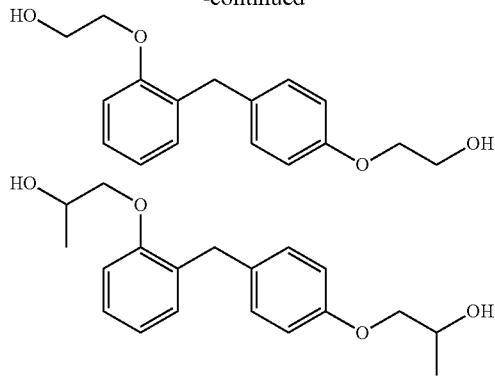

The ethoxylation/propoxylation reaction is generally performed in an alkaline medium at temperatures between 120° C. and 200° C. Generally, the bisphenol F is initially charged, melted and the addition of an alkaline medium in the form of for example potassium carbonate, sodium carbonate, potassium hydroxide, sodium hydroxide, calcium hydroxide, calcium oxide, amines or triphenylphosphine is effected at temperatures up to 180° C. Subsequently ethylene carbonate/propylene carbonate is added and, depending on technical capability, the carbon dioxide formed is discharged. The product fainted need not necessarily be distilled off and may after cooling optionally be neutralized with an acid. A neutral product is preferred in the use as a polyol in polyurethane production. Preference is given to a neutralization for example with a compatible organic (for example benzoic acid phthalic acid, lactic acid, anthranilic acid or salicylic acid) and/or inorganic (for example hydrochloric acid, sulfuric acid, phosphoric acid or nitric acid) acid.

Preference is given to a process for producing the composition according to the invention containing the steps of:
I)
a) addition of bisphenol F into a reactor and melting at temperatures between 120° C. and 160° C.
b) addition of an alkaline medium and heating to 180° C.
c) addition of ethylene carbonate and removal of the carbon dioxide
d) optionally addition of an acid for neutralization
II)
e) addition of bisphenol F into a reactor and melting at temperatures between 120° C. and 160° C.
f) addition of an alkaline medium and heating to 180° C.
g) addition of propylene carbonate and removal of the carbon dioxide
h) optionally addition of an acid for neutralization
III)
combination of the components produced under (I) and (II), preferably in a solvent, to produce the binary mixture.

The molar ratio of bisphenol F:ethoxylating agent/propoxylating agent may be 1:4 to 1:2 for example. The more ethoxylating agent/propoxylating agent was used during the production (for example 1:4) the better was the solubility in various solvents and thus the miscibility with the isocyanate. When a ratio of bisphenol F:ethoxylating agent and/or a ratio of bisphenol F:propoxylating agent of 1:2.0 to 1:2.3, preferably 1:2, was selected the higher aromatics proportion in the polyurethane material further increased the flame retardancy while excellent solubilities in various solvents were retained.

It is generally also possible to perform the production of bisphenol F by reaction of phenol with formaldehyde in a reactor and to undertake the reaction with the ethoxylating agent or propoxylating agent immediately thereafter preferably in the same reaction vessel. This has the advantage that the bisphenol F need not be subjected to storage and may be further used immediately according to requirements.

According to the required separate production of the ethoxylated bisphenol F, and propoxylated bisphenol F these two substances are combined to afford a binary mixture—preferably with stirring—in a weight ratio of 20:80 to 80:20, preferably 30:70 to 70:30, preferably in turn 50:50, preferably in a solvent. However, it is generally also possible to heat and to intimately intermix the ethoxylated bisphenol F and the propoxylated bisphenol F in the specified weight ratio and then optionally add the solvent subsequently.

Surprisingly, the binary mixture shows a very good solubility in solvents particularly compatible with the production of polyurethanes. Thus the binary mixture is very good soluble in for example organo phosphates such as triethylphosphate and diphenylcresyl phosphate, polyether polyols such as ethoxylated sugar, 1,4-butanediol, ethoxylated phenol, ethoxylated cresol or else aromatic polyester polyols, modified or unmodified phenolic resoles (e.g. phenol and cresol based resoles) either alone or mixtures thereof. The resoles can be those that are dissolved in organic solvents.

The propensity for crystallization of the composition according to the invention was surprisingly present only to a very small extent, if at all, compared to solutions containing purely ethoxylated bisphenol F or propoxylated bisphenol F. The binary mixture was preferably added in a weight ratio to the solvent of 80:20 to 20:80, preferably 60:40 to 40:60, preferably in turn 50:50. Particularly at a ratio of binary mixture to solvent of 50:50 the composition according to the invention showed very good storage stability over several weeks in various solvents.

Alkoxylated resorcinol has proven particularly preferable as an exceptional solvent. The term "alkoxylated resorcinol" encompasses substances where the resorcinol has been reacted with at least one alkoxylating agent, thus for example an ethoxylating agent (ethylene oxide, ethylene carbonate) and/or propoxylating agent (propylene oxide, propylene carbonate).

The molar ratio of resorcinol to alkoxylating agent is preferably 1:2 to 1:2.5. Alkoxylated resorcinol comprehends for example the following structure:

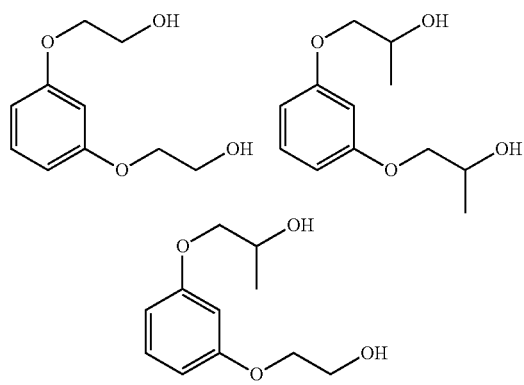

wherein these products are formed mainly in the reaction of resorcinol with ethylene carbonate and propylene carbonate. However, further products may also be formed in It is particularly preferable when a combination of an ethoxylating agent and a propoxylating agent is used as the alkoxylating agent. A product alkoxylated in this way was a more effective solvent of the binary mixture than for example pure propoxylated resorcinol.

The production of the alkoxylated resorcinol may be effected such that the resorcinol is melted and in an alkaline medium in the faun of for example potassium carbonate, sodium carbonate, potassium hydroxide, sodium hydroxide, calcium hydroxide, calcium oxide, amines or triphenylphosphine at elevated temperatures is admixed with a first alkoxylating agent (for example propylene carbonate) and the reaction takes place with removal of carbon dioxide. This may optionally be followed by addition of a further alkoxylating agent (for example ethylene carbonate) at elevated temperature, wherein the carbon dioxide is in turn removed. After appropriate postreaction the product may optionally be distilled off and neutralized with an acid (for example benzoic acid, phthalic acid, lactic acid, anthranilic acid, salicylic acid, hydrochloric acid, sulfuric acid, phosphoric acid and/or nitric acid).

The use of alkoxylated resorcinol is advantageous in particular in the production of polyurethanes since additional difunctional groups which can react with isocyanates are present. At the same time the viscosity of the entire polyol mixture is influenced such that good storage stability results. Furthermore the use of alkoxylated resorcinol increases the aromatic proportion of the polyol component and the flame retardancy and compatibility for example with MDI or the blowing agents was therefore further increased.

It is advantageous in terms of process engineering when during the production of the ethoxylated bisphenol F or propoxylated bisphenol F, resorcinol is ethoxylated and/or propoxylated simultaneously or subsequently utilizing the same reaction vessel.

The ratio of the binary mixture to the alkoxylated resorcinol (ARC) is in the composition according to the invention in the weight ratio 80:20 to 20:80, preferably 60:40 to 40:60, preferably in turn 50:50. For instance, in one embodiment, the ratio of EBF:PBF:ARC could be 25:25:50.

The solubilized binary mixture surprisingly exhibits less propensity for crystallization and forms a storage stable composition which may be used as a polyol component as necessary with di- or polyisocyanates for the production of polyurethanes or polyisocyanurate-based polymers.

It is generally also possible for the composition according to the invention to be used as one polyol component, i.e. for further polyol components, for example polyester polyols, also to be used for the production of polyurethanes or polyisocyanurates. Polyester polyols comprise reaction product of polyols, typically diols, with polycarboxylic acids or their anhydrides, typically dicarboxylic acids or dicarboxylic anhydrides. The polycarboxylic acids or anhydrides may be aliphatic, cycloaliphatic, aromatic and/or heterocyclic.

Mannich base polyols which are synthesized from Mannich bases may also be used as part of the isocyanate-reactive compound.

Preferably employed as isocyanate components are m-phenylene diisocyanate, toluene 2,4-diisocyanate, toluene 2,6-diisocyanate, hexamethylene 1,6-diisocyanate, tetramethylene 1,4-diisocyanate, cyclohexane 1,4-diisocyanat, hexahydrotoluene diisocyanate, naphthylene 1,5-diisocyanat, methoxyphenyl 2,4-diisocyanate, diphenylmethane 4,4'- diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dimethyldiphenylmethane 4,4'-diisocyanate, 4,4',4"-triphenylmethane triisocyanate, a polymethylenepolyphenyl isocyanate, polymeric diphenylmethane diisocyanate (PMDI), isophorone diisocyanate, 2,4,6-toluene triisocyanate and 4,4'-dimethyldiphenylmethane 2,2',5,5'-tetraisocyanate. In different embodiments the polyisocyanate is diphenylmethane 4,4'-diisocyanate, diphenylmethan 2,4-diisocyanate, hexamethylene 1,6-diisocyanate, isophorone diisocyanat, toluene 2,4-diisocyanate, toluene 2,6-diisocyanate or mixtures thereof. Diphenylmethane 4,4'-diisocyanate, diphenylmethane 2,4-diisocyanate and mixtures thereof are generally referred to as MDI. Toluene 2,4-diisocyanate, toluene 2,6-diisocyanate and mixtures thereof are referred to generally as TOI. Each of the above-mentioned polyisocyanates may be modified such that urethane, urea, biuret, carbodiimide, allophanate, uretonimine, isocyanurate, amide or similar moieties are included. Examples of modified isocyanates of this kind comprise various urethane- and/or urea-containing prepolymers and so-called "liquid MDI" products and the like. It is also possible for the polyisocyanate to be a blocked isocyanate.

Depending on the specific type of the produced polymer and the necessary properties of the polymer a great multiplicity of additional materials may be present during the reaction of the polyisocyanate compound with the composition according to the invention. These materials comprise but are not limited to surfactants, blowing agent s, cell openers, fillers, pigments and/or dyes, drying agents, reinforcers, biocides, preservatives, antioxidants, diluents, flame retardants and the like. When a flame retardant is present the flame retardant may be a phosphorus-containing flame retardant. Examples for phosphorus-containing flame retardants comprise but are not limited to triethyl phosphate (TEP), triphenyl phosphat (TPP), trischloroisopropyl phosphate (TCPP), dimethylpropane phosphate, resorcinol bis(diphenyl phosphate) (RDP), Bisphenol-A diphenyl phosphate (BADP) and tricresyl phosphate (TCP), dimethylmethyl phosphonate (DMMP), diphenylcresyl phosphate and aluminium diethyl phosphinate. Examples of diluents comprise polyglycols such as ethylene glycol, glycerol or diethylene glycol, etherified polyglycols such as monomethyl ethers of ethylene glycol or dimethyl ethers of ethylene glycol and dibasic esters of acids such as diethyl adipate, dimethyl adipate, diethyl succinate or dimethyl succinate. Mixtures of these diluents may likewise be used.

The relative amounts of polyisocyanate and composition according to the invention are selected to generate a polymer. The ratio of these components is generally referred to as the "isocyanate index" which is to be understood as meaning 100 times the ratio of isocyanate groups to isocyanate-reactive groups provided by the composition according to the invention. The isocyanate index is generally at least 50 and may be up to 1000 or more. Inflexible polymers such as structural polyurethanes and rigid foams are typically produced using an isocyanate index of 90 to 200. When flexible or semi-flexible polymers are produced, the isocyanate index is generally 70 to 125. Polymers containing isocyanurate groups are often produced with isocyanate indices of at least 150 to 600 or more.

In order to form the polymer, the polyisocyanate compound and the composition according to the invention are mixed and reacted.

In various embodiments the polyisocyanate and the composition according to the invention may optionally also contain a catalysts. Examples of catalysts include but are not limited to tertiary amines, such as dimethylbenzylamine, 1,8-diaza(S,4,0)undec-7-ane, pentamethyldiethylenetriamine, dimethylcyclohexylamine and triethylenediamine.

Potassium salts, such as potassium acetate and potassium octoate, may likewise be used as catalysts.

The composition according to the invention may be used for the production of polyurethanes in particular in the form of prepolymers, foams (rigid, flexible), coatings, lacquers, elastomers, adhesives, sealants and/or composite materials.

The invention shall be more particularly elucidated with reference to an exemplary embodiment:

a) Production of ethoxylated bisphenol F (EBF)
  1. 694.20 kg of bisphenol Fare added into a reactor as a solid and melted at temperatures between 120° C.-160° C.
  2. 1.74 kg of potassium carbonate are subsequently added with stirring at 130° C. and the reaction mixture is heated further to 175° C.-180° C.
  3. 611.60 kg of ethylene carbonate are then added over 5 h with stirring at 175-180° C. Carbon dioxide is liberated. The feed may optionally be prolonged to 10 h depending on technical capability for removing the carbon dioxide.
  4. For the postreaction the temperature is held at 175° C. to 180° C. for 1-2 hours, optionally longer, until no more carbon dioxide is formed and the reaction is complete.
  5. The reaction mixture is cooled to 150° C. and 3.47 kg of salicylic acid are added.
  6. When the product has cooled further (50° C. to 60° C.) it may be discharged into a hobbock without using a filter.

b) Production of propoxylated bisphenol F (PBF)
  1. 632.50 kg of bisphenol Fare added into a reactor as a solid and melted at temperatures between 120° C.-1 G0° C.
  2. 1.58 kg of potassium carbonate are subsequently added with stirring at 130° C. and the reaction mixture is heated further to 175° C.-180° C.
  3. 645.80 kg of propylene carbonate are then added over 5 h with stirring at 175-180° C. Carbon dioxide is liberated. The feed may optionally be prolonged to 10 h depending on technical capability for removing the carbon dioxide.
  4. For the postreaction the temperature is held at 175° C. to 180° C. for 1-3 hours, optionally longer, until no more carbon dioxide is formed and the reaction is complete.
  5. The reaction mixture is cooled to 150° C. and 3.16 kg of salicylic acid are added.
  6. To reduce the content of free propylene carbonate from 0.3% to <0.1% this may optionally be distilled off under vacuum.
  7. When the product has cooled further (S0° C. to 60° C.) it may be discharged into a hobbock without using a filter.

c) Production of the alkoxylated resorcinol (ARC with a molar ratio of resorcinol:propylene carbonate:ethylene carbonate=1:1.0:1.0)
  1. 516.7 kg of resorcinol are added as a solid into a reactor and melted (mp: 111° C.).
  2. 1.31 kg of potassium carbonate are subsequently added with stirring at 130° C. and the reaction mixture is heated further to 175° C.-180° C.
  3. 479.1 kg of propylene carbonate are then added over 2.5 h with stirring at 175-180° C. Carbon dioxide is liberated. The feed may optionally be prolonged to up to 5 h depending on technical capability for removing the carbon dioxide.

4. 413.4 kg of ethylene carbonate are then added over 2.5 h with stirring at 175-180° C. Carbon dioxide is liberated in turn. The feed may optionally be prolonged to 5 h depending on technical capability for removing the carbon dioxide.

5. For the postreaction the temperature is held at 175° C. to 180° C. for 2-6 hours, optionally longer, until no more carbon dioxide is formed and the reaction is complete.

6. The reaction mixture is distilled for a short time under vacuum at 175-180° C.

7. The reaction mixture is cooled to 140° C. and 2.58 kg of salicylic acid are added.

d) Production of the propoxylated resorcinol (molar ratio of resorcinol:propylene carbonate=1:2.0)

The production of the propoxylated resorcinol was effected as described at c) with the exception that 485.1 kg of resorcinol were reacted with 899.6 kg of propylene carbonate using 1.21 kg of potassium carbonate and step 4 was thus eschewed.

The ethoxylated/propoxylated bisphenol F produced at a) and b) was added to the solvents reported in tables 1 and 2. A weight ratio of ethoxylated bisphenol F:propoxylated bisphenol F of 50:50 was selected here.

The weight ratio of this binary mixture to the reported solvent was 80:20 or 50:50. The ethoxylated/propoxylated bisphenol F was introduced into the solvent with stirring and for storage placed into a conditioning cabinet. After the reported time (one week—table 1; 7 weeks—table 2) the samples were withdrawn and evaluated in terms of their crystallization. Due to the consistency of the samples a quantitative analysis of the crystallized product was not possible and determination of the degree of crystallization was therefore effected by visual comparison of the samples with one another. Complete crystallization was recorded as 100% and no crystallization as 0%. The grading of crystallization was subjected to repeated visual determination.

TABLE 1 storage for one week at 20° c. in conditioning cabinet

| | | X | | |
|---|---|---|---|---|
| Solvent | Ratio of x:solvent | Ethoxylated bisphenol F (EBF) | Propoxylated bisphenol F (PBF) Crystallization | 50 EBF:50 PBF invention |
| Triethyl phosphate (TEP) | 80:20 | 100% | 100% | 100% |
| | 50:50 | 100% | 100% | 50% |
| Diethylene glycol (DEG) | 80:20 | 100% | 100% | 50% |
| | 50:50 | 100% | 100% | 0% |
| Ethoxylated sugar (Su-EO) | 80:20 | 100% | 100% | 50% |
| | 50:50 | 100% | 100% | 0% |
| Propoxylated resorcinol (PRC) | 80:20 | 100% | 100% | 0% |
| | 50:50 | 100% | 0% | 0% |
| 1,4-butanediol | 80:20 | 100% | 100% | 50% |
| | 50:50 | 100% | 10% | 10% |
| Ethoxylated phenol | 80:20 | 100% | 100% | 75% |
| | 50:50 | 100% | 100% | 0% |
| Ethoxylated o-cresol | 80:20 | 100% | 100% | 25% |
| | 50:50 | 100% | 100% | 0% |

A number of the samples were stored for additional weeks in the conditioning cabinet at 20° C.

TABLE 2

Storage for 7 weeks at 20° C. in conditioning cabinet

| | | X | | |
|---|---|---|---|---|
| Solvent | Ratio of x:solvent | Ethoxylated bisphenol F (EBF) | Propoxylated bisphenol F (PBF) Crystallization | 50 EBF:50 PBF invention |
| Diethylene glycol (DEG) | 50:50 | 100% | 100% | 75% |
| Ethoxylated sugar (Su-EO) | 50:50 | 100% | 100% | 10% |
| Propoxylated resorcinol (PRC) | 50:50 | 100% | 50% | 0% |
| Ethoxylated phenol | 50:50 | 100% | 100% | 50% |
| Ethoxylated o-cresol | 50:50 | 100% | 100% | 10% |

Since the crystallization of the binary mixture surprisingly occurs only to a limited extent even after a relatively long time it is apparent that the composition according to the invention is storage stable over a relatively long period. The viscosity of the composition according to the invention also remains virtually unchanged on account of the low propensity for crystallization and said composition therefore exhibits good compatibility with the isocyanate when used as a polyol component. As a result of the high aromatic proportion of the binary mixture and optionally also as a result of the use of propoxylated resorcinol which further increases the aromatic proportion, a good flame retardancy in the polyurethane end product was achieved and the compatibility with MDI/with the blowing agents was further increased as well. The additional use of halogenated flame retardants was accordingly eschewed.

What is claimed is:

1. A composition comprising
   ethoxylated bisphenol F and
   propoxylated bisphenol F in a weight ratio of 20:80 to 80:20.

2. The composition of claim 1, wherein the ethoxylated bisphenol F is obtained by reaction of bisphenol F and ethylene carbonate.

3. The composition of claim 1, wherein the propoxylated bisphenol F is obtained by reaction of bisphenol F and propylene carbonate.

4. The composition of claim 1, wherein a molar ratio of bisphenol F:ethoxylating agent is at least 1:2 and/or a molar ratio of bisphenol F:propoxylating agent is at least 1:2.

5. The composition of claim 1, wherein the weight ratio of ethoxylated bisphenol F to propoxylated bisphenol F is 30:70 to 70:30.

6. The composition of claim 1, further comprising an alkoxylated resorcinol.

7. The composition of claim 6, wherein the alkoxylated resorcinol is produced by reaction of resorcinol with a combination of ethoxylating agent and propoxylating agent.

8. The composition of claim 6, wherein the ethoxylated bisphenol F and propoxylated bisphenol F form a binary mixture and wherein a weight ratio of the binary mixture to the alkoxylated resorcinol is 80:20 to 20:80.

9. A process comprising:
   I)
   a) adding bisphenol F into a reactor and melting at temperatures between 120° C. and 160° C.
   b) adding an alkaline medium and heating to 180° C.
   c) adding ethylene carbonate and removal of the carbon dioxide
   d) optionally adding an acid for neutralization, II)
- e) adding bisphenol F into a reactor and melting at temperatures between 120° C. and 160° C. f) adding an alkaline medium and heating to 180° C.
- g) adding propylene carbonate and removal of the carbon dioxide
- h) optionally adding an acid for neutralization, and III) combining the components produced under (I) and (II), to provide a binary mixture having a I:II weight ratio of 20:80 to 80:20.

10. A polyurethane or a polyisocyanurate made from the composition of claim 1.

11. A prepolymer, foam, insulation material, coating, lacquer, elastomer, adhesive, sealant and/or composition material comprising polyurethane or the polyisocyanurate of claim 10.

* * * * *